US006146902A

United States Patent [19]
McMaster

[11] Patent Number: 6,146,902
[45] Date of Patent: Nov. 14, 2000

[54] PURIFICATION OF POLYSACCHARIDE-PROTEIN CONJUGATE VACCINES BY ULTRAFILTRATION WITH AMMONIUM SULFATE SOLUTIONS

[75] Inventor: Ronald McMaster, Stroudsburg, Pa.

[73] Assignee: Aventis Pasteur, Inc., Swiftwater, Pa.

[21] Appl. No.: 09/221,728

[22] Filed: Dec. 29, 1998

[51] Int. Cl.$^7$ .............................. G01N 1/18; C07G 17/00; A61K 39/385
[52] U.S. Cl. .................... 436/177; 536/127; 424/197.11; 424/193.1
[58] Field of Search ............................ 436/177; 435/276, 435/961; 424/193.1, 236.1, 197.11; 530/807, 816, 412, 418, 419; 536/127

[56] References Cited

U.S. PATENT DOCUMENTS

| | | | |
|---|---|---|---|
| 4,456,691 | 6/1984 | Stark | 436/543 |
| 4,780,409 | 10/1988 | Monji et al. | 435/7 |
| 5,122,614 | 6/1992 | Zalipsky | 548/520 |
| 5,153,312 | 10/1992 | Porro | 530/405 |

FOREIGN PATENT DOCUMENTS

| | | |
|---|---|---|
| 0477508B1 | 4/1992 | European Pat. Off. . |
| 0497525 | 8/1992 | European Pat. Off. . |
| 0665020 | 8/1995 | European Pat. Off. . |
| WO 92/04915 | 4/1992 | WIPO . |

OTHER PUBLICATIONS

Concise Encyclopedia Chemistry, (Eds) Jacubke et al., Walter de Gruyter Berlin, New York, p. 876, 1994.
Whitfiled et al. J. Bacteriol. 174: 4913–4919, 1992.
Zalipsky et al. Biotechnol. Appl. Biochem. 15: 100–114, 1992.
Muzykantov et al. Anal. Biochem. 169: 383–389, 1988.
Chuet al., (1991) *Infect. Immun.*, vol. 59, pp. 4450–4458.
Bartlett, (1959) *Journal of Biological Chemistry*, vol. 234, pp. 466.
Lowry et al., (1951) *Journal of Biological Chemistry*, vol. 193, pp. 265.
Aragon et al., (1993) *Vaccine*, vol. 11, pp. 552–557.
Isbell et al., (1987) *Carbohydrate Research*, vol. 161, pp. 181–193.
Park et al., (1949) *J. Biol. Chem.*, vol. 181, pp. 149.
Dick et al., (1989) *Conjugate Vaccines. Contrib. Microbiol. Immunol.*, vol. 10, pp. 48–114.

*Primary Examiner*—James C. Housel
*Assistant Examiner*—S. Devi
*Attorney, Agent, or Firm*—Timothy R. Howe; G. Kenneth Smith; Aventis Pasteur, Inc.

[57] ABSTRACT

Disclosed and claimed are a method for the purification of polysaccharide-protein conjugate vaccines by ultrafiltration in a saturated solution of ammonium sulfate. The ultrafiltration method of the present invention provides an efficient, readily scalable method for removal of unbound polysaccharides from polysaccharide-protein vaccines, thereby improving the purity and consistency of the polysaccharide-protein vaccines.

13 Claims, 1 Drawing Sheet

FIGURE 1

Wash out kinetics of adipic acid dihydrazide derivatized *Neisseria meningitidis* serogroup C from a conjugation reaction mixture ultrafiltered against 10 volumes of 50% (of saturation) ammonium sulfate using a Millipore Prep/Scale 30,000 MWCO spiral wound fitted with a regenerated cellulose membrane.

Removal of Free PS by Ultrafiltration

PURIFICATION OF POLYSACCHARIDE-PROTEIN CONJUGATE VACCINES BY ULTRAFILTRATION WITH AMMONIUM SULFATE SOLUTIONS

FIELD OF THE INVENTION

The present invention relates to the removal of unbound polysaccharides from conjugated polysaccharide-protein vaccines using the method of ultrafiltration whereby the diafiltration solution contains saturating levels of ammonium sulfate.

Several publications are referenced in this application. Full citation to these publications is found where cited or at the end of the specification, immediately preceding the claims; and each of these publications is hereby incorporated by reference. These publications relate to the state of the art to which the invention pertains; however, there is no admission that any of these publications is indeed prior art.

BACKGROUND OF THE INVENTION

In recent years, a number of polysaccharide-protein conjugate vaccines have been developed for use in protection against bacterial infections. One such vaccine, the *Haemophilus influenzae* type B conjugate vaccine is now licensed for use in humans throughout the world. This vaccine is administered to infants along with their other routine pediatric vaccines. The *Haemophilus influenzae* type B conjugate vaccine has proven to be quite effective in protecting against *Haemophilus influenzae* type B disease (Santosham, M., 1993). The polysaccharide-protein conjugate vaccines are prepared by covalently attaching purified bacterial capsular polysaccharides to protein molecules using a variety of chemical methods. Upon completion of the conjugation reactions, the unreacted polysaccharide molecules are separated from the polysaccharide-protein conjugates using an assortment of separation techniques. The techniques that have been proven to be most effective in purifying the polysaccharide-protein conjugates include gel filtration chromatography, hydrophobic interaction chromatography, ultracentrifugation, liquid-liquid extraction, and ammonium sulfate precipitation/fractionation.

The reason for the interest in developing conjugate vaccines is that these vaccines are capable of eliciting an anti-polysaccharide specific immune response that protects against disease. These polysaccharide-conjugate vaccines protect against pathogens that contain an outer polysaccharide shell. These vaccines have proven to be effective in protecting infants and young children against disease. The reason why these vaccines are effective in younger populations is due to the conversion of the purified bacterial capsular polysaccharides, which are classified as T-cell independent antigens, into T-cell-like antigens when they are covalently attached to certain protein molecules. T-cell antigens are capable of eliciting an immune response that can be boosted upon subsequent vaccination thereby allowing one to establish a level of protection in the vaccinated subject. These T-cell antigens normally confer long lasting immunity against disease. The purified bacterial capsular polysaccharides are capable of eliciting an immune response in man. However, the immune response can be of limited duration, especially in younger populations. The immune response in younger populations is normally very low, and is considered not to be of a protective level. Subsequent vaccinations with polysaccharide does not normally yield a higher, or boosted, antibody response, because there is no T-cell help, or memory antibody. For this reason, the polysaccharide vaccines have not been recommended for use in infant populations, and children younger than 2 years of age.

In preparation of the polysaccharide-protein conjugate vaccines, steps are normally taken to remove the unbound polysaccharide from these preparations because the unbound polysaccharide does not provide any benefit to the vaccinated subject. In addition, there has been an increased effort to develop well-characterized vaccines that are of a higher degree of purity for licensure.

OBJECTS AND SUMMARY OF THE INVENTION

Ultrafiltration, like dialysis, is based on the principle of separating molecules according to size using a semipermeable membrane of a defined range of pore sizes. Ultrafiltration is widely used in protein and polysaccharide purification for concentrating protein and polysaccharide molecules and for changing the composition of the buffer solution. Ultrafiltration is also used in polysaccharide and protein purification for removing low-molecular-weight solutes from these sample solutions. This process technique is routinely applied in small laboratory experiments and in manufacturing scale process steps.

The object of this invention is to provide a method of separating unreacted or unbound polysaccharide from polysaccharide-protein conjugate preparations based upon the difference in molecular size. The unreacted or unbound polysaccharide, although relatively large in molecular size, 1,000 to 50,000 daltons, are much smaller than the molecular size of the polysaccharide-protein conjugate molecules, that range from 100,000 to 1,000,000 daltons in molecular size. In developing this method for polysaccharide-protein conjugate purification, the invention provides the opportunity for ease of scale-up to industrial size reaction preparations.

Polysaccharide and protein molecules do not behave the same with respect to their relative ease of passing through semipermeable membranes. One reason for this is that polysaccharides exist as molecular size distributions whereas proteins are normally of a defined molecular size. Proteins exist in solution as bead-like structures, whereas polysaccharides may adopt a variety of conformations (e.g. helical coils) or they can exist as random string-like structures. As a result of the various geometric forms that polysaccharides can adopt in solution, some polysaccharides may pass through semipermeable membranes more easily than others. The chemical make up of the semipermeable can be either hydrophobic (e.g. polyether sulfone) or hydrophilic (e.g. regenerated cellulose) in nature. The chemical make-up of the semipermeable membrane can influence the ease with which proteins and polysaccharide pass through the pores. Polysaccharides of molecular size 1 to 50,000 can pass through semipermeable membranes whose pore size has a molecular size cutoff of 30,000 using 0.15 M sodium chloride solution as the diafiltration buffer. When a mixture of the same polysaccharide and polysaccharide-protein conjugates are subjected to the same ultrafiltration experimental conditions, very little of the unbound polysaccharide will pass through the semipermeable membrane. However, when the diafiltration buffer is changed to 40% (of saturation) ammonium sulfate, then the unbound polysaccharide freely passes through the membrane pores.

While ammonium sulfate is the preferred salt to use in the method of the present invention, those skilled in the art will recognize that potassium or sodium phosphates or sulfates, ammonium acetate, ammonium phosphate and other stronger salts in the Hofmeister series can be used in place of ammonium sulfate, with comparable results. It is to be understood that, for purposes of the present invention, the terms "saturating salt solution" and "ammonium sulfate solution" are used interchangebly.

The saturating salt solution does not affect the size of the membrane pores. The level of saturation does play an important role in allowing the unbound polysaccharide to freely pass through the semipermeable membrane. Below 40% (of saturation) very little unbound polysaccharide will pass through the membrane, however, above 40% (of saturation) the polysaccharide freely elutes through the membrane pores. This invention does not require that the polysaccharide-protein conjugate precipitate out of solution for it to work. The method works equally well whether or not the polysaccharide-protein conjugate is fully solubilized or precipitated from solution. Proper selection of the appropriate membrane pore size and percent saturation of ammonium sulfate, allows for high yield recovery of the desired polysaccharide-protein conjugate while allowing for the removal of unreacted polysaccharide.

As to membranes, examples are provided in which hydrophobic as well as hydrophilic membranes have been used, with comparable results. Such membranes can be used as flat sheets or, preferably, in a spiral wound configuration. Hollow fiber can also be used. Any number of potential membrane materials can be used including, by way of example and not limitation, regenerated cellulose, polyether sulfone (which may or may not be modified to alter its inherent hydrophobicity) and polyvinylidene fluoride.

The present invention provides a gentle means for the purification of polysaccharide-protein conjugates that is readily scaleable to any size reaction volume. Of course, the method of the present invention will apply equally well to any purification application in which a purified protein is to be separated from one or more of another molecular species (such as saccharides, nucleic acids and lipoproteins).

One method of purification that can be performed at large scale volumes is to precipitate the polysaccharide-protein conjugate from solution using ammonium sulfate. In this process, the unbound polysaccharide remains in solution, however, there are certain drawbacks with this approach. In order to achieve the same level of purity that is provided by the present invention, one needs to perform repetitive ammonium sulfate precipitations due to some partitioning of the polysaccharide with the precipitated polysaccharide-protein conjugate. Certain polysaccharide-protein conjugates are difficult to resolubilize once they are precipitated from solutions. In the present invention, the method does not require that the polysaccharide-protein conjugate be precipitated out of solution. The ammonium sulfate diafiltration solution disrupts any potential interaction or association between the unbound polysaccharide and the polysaccharide-protein conjugate.

The invention provides a method for purifying polysaccharide-protein conjugates to a level that contain less than 1% unbound polysaccharide by weight.

The invention provides a method for purifying polysaccharide-protein conjugates that have been prepared from bacterial capsular polysaccharides from *Streptococcus pneumoniae* serotypes 1, 3, 5, 6B, 7F, 9V, 14, 18C, 19F, 23F and from *Neisseria meningitidis* serogroups A, C, W-135 and Y.

The invention provides a method for purifying a polysaccharide-protein conjugate so as to preserve an epitope of interest, a biological response modulator, and/or a growth factor, such that the present invention provides an immunological and/or vaccine or therapeutic agent.

The invention further provides a purified polysaccharide-protein conjugate vaccine that may be administered to an animal or human in order to obtain an immunological or protective immune response or for treatment or therapy.

BRIEF DESCRIPTION OF THE FIGURES

FIG. 1 shows washout kinetics of adipic acid dihydrazide derivatized *Neisseria meningitidis* serogroup C from a conjugation reaction mixture ultrafiltered against 10 volumes of 50% (of saturation) ammonium sulfate using a Millipore Prep/Scale 30,000 MWCO spiral wound fitted with a regenerated cellulose membrane. Removal of free polysaccharide (PS) by ultrafiltration is displayed graphically as Filtrate ug PS/ml vs. Volumes Ammonium Sulfate Diafiltered.

DETAILED DESCRIPTION OF THE INVENTION

The invention has been applied to purify a number of distinctly different polysaccharide-protein conjugates that are derived from a variety of bacterial capsular polysaccharides, although the invention need not be limited to only these polysaccharide-protein conjugates. The bacterial capsular polysaccharide-protein conjugates that have been purified by this process include *Streptococcus pneumoniae* serotypes 1, 3, 5, 6B, 7F, 9V, 14, 18C, 19F, and 23F, and *Neisseria meningitidis* serogroups A, C, W-135 and Y. Such polysaccharides are available from the American Type Culture Collection, or can be readily obtained from any of a number of potential sources. For example, such polysaccharides can be extracted and purified directly from microorganisms. See, e.g., Porro, U.S. Pat. No. 5,153,312 and EP 0477508 B1 for a discussion of such preparation procedures. The polysacharides may also be partially depolymerized or fragmented, using chemical or mechanical means, some of which are detailed by Porro. Hagopian et al. EP 497,525 and references cited therein also provide guidance as to methods of preparing and characterizing polysaccharides. See also, Chu, et. Al. (1991) Infect. Immun. 59: 4450–4458 for a description of lipopolysaccharide-based conjugate vaccines.

According to the method of the present invention, the derivatized polysaccharide is first mixed with the protein carrier of choice in a solution of physiological saline (0.85% sodium chloride), and the pH of the mixture is adjusted to 5.0±0.1. The conjugation reaction is initiated by adding 1-ethyl-3-(3-dimehtylaminopropyl) carbodiimide (EDAC) which serves to activate the carboxyl groups on the carrier protein allowing for reaction from a nucleophilic site that is present on the polysaccharide chain. The pH of the reaction is maintained at 5.0±0.1 during the course of the reaction, normally for two hours at 18 to 25° C. After the reaction time is complete, the pH of the reaction mixture is adjusted to 7.0±0.1, and the reaction is allow to stand for 12 to 18 hours at 2 to 8° C. to allow for hydrolysis of the unreacted EDAC.

The polysaccharide-protein conjugate is purified by first allowing the mixture to equilibrate to 18 to 25° C. The mixture is connected to a spiral wound ultrafiltration unit that is equipped with a Millipore Prep/Scale 30,000MWCO regenerated cellulose membrane. Ammonium sulfate is added to the reaction mixture at a specified level of saturation (in general, 50 to 60% of saturation). The conjugate mixture is diafiltered against 20 volume exchanges of 50 to 60% (of saturation) ammonium sulfate solution. The ammonium sulfate is removed from the polysaccharide-protein solution by diafiltration against 10 volume exchanges of physiological saline (0.85% sodium chloride). The purified conjugate is filtered through 1.2 and 0.45 micron membranes, and then sterilized by filtration through a 0.22 micron membrane.

The invention is dependent upon the presence of ammonium sulfate in the diafiltration wash buffer. This invention was discovered from the following set of experiments that are described below.

A conjugation reaction was performed using purified *Neisseria meningitidis* serogroup C that had been derivatized with adipic acid dihydrazide with diphtheria toxoid protein. A portion of this reaction mixture was purified by three successive ammonium sulfate precipitations using at 50% of saturation. The precipitations were performed by first adjusting the pH of the mixture to 7.0±0.1 using dilute sodium hydroxide. Solid ammonium sulfate was added slowly over a 10 minute interval to reach a final concentration of 50% of saturation. The solution was allowed to stand at room temperature for 15 minutes. The precipitated polysaccharide-protein conjugate was collected by centrifugation, using a Beckman JA-20 rotor, at 10,000 rpm at 4° C. The supernatant containing solubilized unreacted polysaccharide was removed, and the protein pellet was dissolved into physiological saline, 0.85% sodium chloride. The pH was adjusted to 7.0±0.1 and the polysaccharide-protein conjugate was precipitated as above. Following the third ammonium sulfate precipitate, the polysaccharide-protein conjugate was dialyzed against physiological saline, 0.85% sodium chloride. The purified conjugate was filtered through 1.2 and 0.45 micron membranes, and then sterilized by filtration through a 0.22 micron membrane. This sample was analyzed for protein, sialic acid content, and for the content of unbound polysaccharide. The remaining portion of the reaction mixture was subjected to a number of ultrafiltration methods of purification. The summary of these purification methods is reported in Table 1.

In the first approach, the remaining reaction mixture was connected to a screen channel minisette ultrafiltation unit equipped with a Filtron 30,000 MWCO polyether sulfone membrane. The conjugation reaction mixture was diafiltered against 10 volumes of physiological saline, 0.85% sodium chloride. A sample of this material was analyzed for protein and sialic acid content, see Table 1.

In a second approach, a portion of the retentate from the physiological saline diafiltered reaction mixture was connected to a screen channel minisette ultrafiltration unit that was equipped with a Filtron 30,000 MWCO polyether sulfone membrane. The mixture was diafiltered against 10 volumes of 1 M sodium chloride, followed by 10 volumes of physiological saline, 0.85% sodium chloride. A sample of this material was analyzed for protein and sialic acid content, see Table 1.

In a third approach, a second portion of the retentate from the physiological saline diafiltered reaction mixture was connected to a screen channel minisette ultrafiltration unit that was equipped with a Filtron 30,000 MWCO polyether sulfone membrane. To this mixture was added solid ammonium sulfate to a concentration of 20% of saturation. The mixture was diafiltered against 7 volumes of 20% (of saturation) ammonium sulfate, followed by 6 volumes of physiological saline, 0.85% sodium chloride. A sample of this material was analyzed for protein and sialic acid content see Table 1.

In a fourth approach, the retentate from the 20% (of saturation) ammonium sulfate diafiltration reaction mixture was connected to a open channel minisette ultratilftration unit that was equipped with a Filtron 30,000 MWCO polyether sulfone membrane. To this mixture was added solid ammonium sulfate to a concentration of 50% of saturation. The mixture was diafiltered against 5 volumes of 50% (of saturation) ammonium sulfate, followed by 6 volumes of physiological saline, 0.85% sodium chloride. A sample of this material was analyzed for protein and sialic acid content, see Table 1.

In a fifth approach, the retentate from the 50% (of saturation) ammonium sulfate diafiltration reaction mixture was connected to a spiral wound ultrafiltration unit that was equipped with a Millipore Prep/Scale 30,000 MWCO regenerated cellulose membrane. The Prep/Scale spiral wound filter cartridge allows one to perform this operation at a higher flux than is obtained with the flat sheet minisette ultrafiltration system. The mixture was diafiltered against 10 volumes of 50% (of saturation) ammonium sulfate, followed by 10 volumes of physiological saline, 0.85% sodium chloride. A sample was analyzed for protein, sialic acid content, and for the content of unbound polysaccharide, see Table 1.

The results from the fourth and fifth experiments showed that inclusion of ammonium sulfate in the diafiltration wash solution allowed for the wash out of the unbound polysaccharide. These experiments were confirmed by performing a follow-up experiment using a new reaction mixture of *Neisseria meningitidis* serogroup C with diphtheria toxoid protein. The conjugation reaction mixture was performed as described above. After overnight incubation at 2–8° C., the reaction mixture was connected to a spiral wound ultrafiltration unit that was equipped with a Millipore Prep/Scale 30,000 MWCO regenerated cellulose membrane. The mixture was diafiltered against 10 volumes of 50% (of saturation) ammonium sulfate. The permeate was tested for sialic acid content on each volume wash. The kinetic profile for the unbound polysaccharide removed is shown in FIG. 1. Following the diafiltration against 50% (of saturation) ammonium sulfate, the polysaccharide-protein conjugate was diafiltered against 10 volumes of physiological saline, 0.85% sodium chloride. The sample was analyzed for protein, sialic acid content, and for the content of unbound polysaccharide, see Table 2.

This invention has been applied in the purification of a number of different polysaccharide-protein conjugate vaccines of which a non-inclusive listing is presented in Table 3. A better understanding of the present invention and of its many advantages will be had form the following non-limiting Examples, given by way of illustration.

EXAMPLES

Example 1

Ultrafiltration purification of *Neisseria meningitidis* serogroup A diphtheria toxoid protein conjugate.

Materials used in the conjugation reaction and the ultrafiltration purification of the polyaccharide-protein conjugate include adipic acid dihydrazide derivatized serogroup A polysaccharide, diphtheria toxoid protein, 1-ethyl-3-(3-dimehtylaminopropyl) carbodiimide (EDAC), physiological saline (0.85% sodium chloride), 0.1 N hydrochloric acid, 0.1 N sodium hydroxide, and ammonium sulfate.

The adipic acid dihydrazide derivatized serogroup A polysaccharide (at 6.5 mg/ml) was mixed with diphtheria toxoid protein (at 5 mg/ml) and the pH of the mixture was adjusted to 5.0±0.1 using 0.1 N hydrochloric acid. The reaction was initiated by adding 1-ethyl-3-(3-dimehtylaminopropyl) carbodiimide (EDAC) to a concentration of 3 mg/ml. The of the reaction mixture was maintained at 5.0±0.1 for two hours. After two hours, the pH of the reaction mixture was adjusted to 7.0±0.1 using 0.1 N sodium hydroxide. The reaction mixture was incubated at 2–8° C. for 18 hours.

Following incubation at 2–8° C., the reaction mixture was allowed to equilibrate to 15 to 30° C., and the pH was adjusted to 7.0±0.1, if necessary. To the reaction mixture was added solid ammonium sulfate over a 10 minute interval to attain a concentration of 60% of saturation. The mixture was connected to a spiral wound ultrafiltration unit that was equipped with a Millipore Prep/Scale 30,000 MWCO regenerated cellulose membrane. The conjugate mixture was diafiltered against 20 volumes of 60% (of saturation) ammonium sulfate solution. The ammonium sulfate was removed from the polysaccharide-protein solution by diafiltration against 10 volume exchanges of physiological saline, 0.85% sodium chloride. The purified conjugate was filtered through 1.2 and 0.45 micron membranes, and then sterilized by filtration through a 0.22 micron membrane.

The quantity of polysaccharide was determined by assaying for phosphorus by the method of Bartlett, G. R. J. (1959) Journal of Biological Chemistry, 234, 466. The quantity of protein was determined by the method of Lowry, O. H., et. al. (1951) Journal of Biological Chemistry 193, 265. The quantity of unbound polysaccharide was measured by passage of the polysaccharide-protein conjugate through a phenyl sepharose CL-6B resin using 1 M ammonium sulfate solution, and by quantitating the amount the unbound and bound polysaccharide by the phosphorus method.

The same method has been used to purify polysaccharide-protein conjugates prepared from *Neisseria meningitidis* serogroups C, W-135 and Y, and from *Streptococcus pneumoniae* serotypes 1, 6B, 7F, 14, and 18C. The difference in the methods used for these other polysaccharide-protein conjugates is the amount of ammonium sulfate that is added to the conjugate reaction mixture, and the concentration of ammonium sulfate in the diafiltration wash buffer.

REFERENCES

1. Santosham, M. (1993) Vaccine 11: 552–557.
2. Bartlett, G. R. J. (1959) Journal of Biological Chemistry 234: 466.
3. Lowry, O. H., et.al. (1951) Journal of Biological Chemistry 193: 265.
4. Isbell, H. S. and Frush, H. L. (1987) Carbohydrate Research 161: 181–193.
5. Park, J. T. and Johnson, M. J. (1949). J. Biol. Chem. 181: 149.
6. Dick, W. E. Jr. and Beurret, M. *Conjugate Vaccines. Contrib. Microbiol. Immunol.* (1989) 10 pgs 48–114. Cruse, J. M. and Lewis, R. E., Jr. eds., Basel, Karger.

TABLE 1

Purification assessment of *Neisseria mengiditis* serogroup C polysaccharide-protein conjugates by ultrafiltration versus the method of ammonium sulfate precipitation.

| Method of Purification | Sialic Acid Content of retentate | Protein Content of retentate | Ratio of Sialic/Protein |
| --- | --- | --- | --- |
| 3 Ammonium sulfate ppts. + dialysis | 0.78 mg/ml | 6.42 mg/ml | 0.12 |
| 10 vol. 0.85% NaCl dialfiltration | 1.85 mg/ml | 0.88 mg/ml | 2.10 |
| 10 vol. 1 M NaCl + 10 vol. 0.85% NaCl diafiltraton (scm)* | 1.89 mg/ml | 1.05 mg/ml | 1.80 |
| 7 vol. 20% Am. Sulf. + 6 vol. 0.85% NaCl diafiltration (scm)* | 1.44 mg/ml | 0.74 mg/ml | 1.95 |
| 5 vol. 50% Am. Sulf. + 6 vol. 0.85% NaCl diafiltration (ocm)* | 0.42 mg/ml | 0.50 mg/ml | 0.84 |
| 10 vol. 50% Am. Sulf. + 10 vol. 0.85% NaCl diafiltration (sw)* | 0.067 mg/ml | 0.35 mg/ml | 0.19 |

*Note: scm = screen channel minisette, ocm = open channel minisette, and spw = spiral wound cartridge.

TABLE 2

Purification of a *Nesseria meningitidis* Serogroup C Polysaccharide-Protein Conjugate using a spiral wound ultrafiltration unit equipped with a Millipore Prep/Scale 30,000 MWCO regenerated cellulose membrane.

| Ultrafiltration Conditions | Sialic acid content of the retentate | Protein content of the retentate | Sialic Acid Protein | % Unbound Polysaccharide in the retentate |
| --- | --- | --- | --- | --- |
| 10 vol. 50% Am. Sulf. + 10 vol/ 0.85% NaCl diafiltration (sw)* | 0.33 mg/ml | 1.89 mg/ml | 0.17 | 7.4% |

TABLE 3

Purification results on polysaccharide-protein conjugates using a spiral wound ultrafiltration unit equipped with a Millipore Prep/Scale 30,000 MWCO regenerated cellulose membrane against 20 volumes of saturated ammonium sulfate solutions, followed by 10 volume exchanges against physiological saline, 0.85% sodium chloride.

| Conjugate | Lot Number | % of Saturation of Ammonium Sulfate | % unbound polysaccharide |
| --- | --- | --- | --- |
| N. men. A | D01886 | 60% | 4.9% |
| N. men C | D01887 | 50% | 7.2% |
| N. men W-135 | D01889 | 60% | 3.2% |
| N. men Y | D01880 | 60% | 6.0% |
| S. pneu 1 | D01905 | 60% | 5.3% |
| S. pneu 6B | 4291PD | 60% | 1.4% |
| S. pneu 7F | D01906 | 60% | 4.4% |
| S. pneu 14 | D01905 | 70% | 11.0% |
| S. pneu 18C | 4292PD | 60% | <1.0% |

What is claimed is:

1. A method for removal of unbound polysaccharide from protein-polysaccharide conjugate in a mixture of protein-polysaccharide conjugate and unbound polysaccharide in solution, the method comprising adjusting the salt concentration of the solution followed by filtration of the mixture through a semi-permeable membrane to separate said unbound polysaccharide from said protein-polysaccharide conjugate, wherein the salt concentration is adjusted so as to permit passage of the unbound polysaccharide through the semi-permeable membrane without precipitating the protein-polysaccharide conjugate.

2. The method of claim 1, wherein the semi-permeable membrane is hydrophobic.

3. The method of claim 2, wherein the hydrophobic membrane is comprised of polyether sulfone.

4. The method of claim 3, wherein the polyether sulfone membrane has a molecular weight cutoff of 30,000.

5. The method of claim 1, wherein the semi-permeable membrane is hydrophilic.

6. The method of claim 5, wherein the hydrophilic membrane is comprised of regenerated cellulose.

7. The method of claim 6, wherein the regenerated cellulose has a molecular weight cutoff of 30,000.

8. The method of claim 1, wherein the salt solution is comprised of ammonium sulfate.

9. The method of claim 8, wherein the ammonium sulfate is present at 20 to 60% of saturation.

10. The method of claim 1, wherein the protein is diphtheria toxoid.

11. The method of claim 1, wherein the polysaccharide is capsular polysaccharide from bacteria selected from the group consisting of *Streptococcus pneumoniae* serotypes 1, 3, 5, 6B, 7F, 9V, 14, 18C, 19F and 23F, and *Neisseria meningitidis* serogroups A. C. and W-135.

12. The method of claim 1 wherein the mixture after filtration through the semi-permeable membrane comprises less than 5% unreacted polysaccharide.

13. The method of claim 1 wherein the mixture after filtration through the semi-permeable membrane comprises less than 1% unreacted polysaccharide.

* * * * *